US011117850B2

United States Patent
Fukuchi et al.

(10) Patent No.: US 11,117,850 B2
(45) Date of Patent: Sep. 14, 2021

(54) METHOD FOR PRODUCING HEXAFLUORO-1,3-BUTADIENE

(71) Applicant: SHOWA DENKO K.K., Tokyo (JP)

(72) Inventors: Yohsuke Fukuchi, Tokyo (JP); Shinya Oguro, Tokyo (JP); Nozomi Inoue, Tokyo (JP)

(73) Assignee: SHOWA DENKO K.K., Tokyo (JP)

(*) Notice: Subject to any disclaimer, the term of this patent is extended or adjusted under 35 U.S.C. 154(b) by 0 days.

(21) Appl. No.: 17/046,037

(22) PCT Filed: Jun. 3, 2019

(86) PCT No.: PCT/JP2019/022045
§ 371 (c)(1),
(2) Date: Oct. 8, 2020

(87) PCT Pub. No.: WO2019/244612
PCT Pub. Date: Dec. 26, 2019

(65) Prior Publication Data
US 2021/0040021 A1    Feb. 11, 2021

(30) Foreign Application Priority Data

Jun. 22, 2018 (JP) .............................. JP2018-118561

(51) Int. Cl.
*C07C 17/23* (2006.01)
*C07C 21/20* (2006.01)
*C07C 21/18* (2006.01)
*C07C 21/19* (2006.01)
*B01J 23/06* (2006.01)

(52) U.S. Cl.
CPC ............... *C07C 17/23* (2013.01); *B01J 23/06* (2013.01); *C07C 21/20* (2013.01)

(58) Field of Classification Search
None
See application file for complete search history.

(56) References Cited

U.S. PATENT DOCUMENTS

| 4,654,448 A | 3/1987 | Bargigia |
| 2009/0216053 A1 | 8/2009 | Ohno et al. |
| 2010/0280291 A1 | 11/2010 | Tortelli et al. |

FOREIGN PATENT DOCUMENTS

| CN | 101910096 A | 12/2010 |
| EP | 3 632 883 A1 | 4/2020 |
| JP | 62-26240 A | 2/1987 |
| JP | 2001-192347 A | 7/2001 |
| JP | 5005681 B2 | 8/2012 |
| WO | 2005/023734 A1 | 3/2005 |
| WO | 2018/216426 A1 | 11/2018 |

OTHER PUBLICATIONS

International Preliminary Report on Patentability dated Dec. 22, 2020 from the International Bureau in International Application No. PCT/JP2019/022045.
R. N. Haszeldine, "Fluoro-olefins, Part I, The synthesis of hexafluorobuta-1,3-diene.", Journal of the Chemical Society, Nov. 1952, pp. 4423-4431, 11.
International Search Report for PCT/JP2019/022045, dated Aug. 13, 2019.

*Primary Examiner* — Medhanit W Bahta
(74) *Attorney, Agent, or Firm* — Sughrue Mion, PLLC

(57) ABSTRACT

Provided is a method for producing hexafluoro-1,3-butadiene, and the method can produce hexafluoro-1,3-butadiene at an industrially sufficient level of yield. In a reaction liquid containing a halogenated butane represented by chemical formula, $CF_2X^1$—$CFX^2$—$CFX^3$—$CF_2X^4$ ($X^1$, $X^2$, $X^3$, and $X^4$ are each independently a halogen atom other than a fluorine atom), zinc, and an organic solvent, a reaction is conducted to eliminate the halogen atoms other than a fluorine atom, $X^1$, $X^2$, $X^3$, and $X^4$, from the halogenated butane, yielding hexafluoro-1,3-butadiene. During the reaction, the concentration of a zinc halide generated by the reaction, in the reaction liquid is not more than the solubility of the zinc halide in the organic solvent.

9 Claims, No Drawings

METHOD FOR PRODUCING HEXAFLUORO-1,3-BUTADIENE

CROSS REFERENCE TO RELATED APPLICATIONS

This application is a National Stage of International Application No. PCT/JP2019/022045 filed Jun. 3, 2019, claiming priority based on Japanese Patent Application No. 2018-118561 filed Jun. 22, 2018.

TECHNICAL FIELD

The present invention relates to a method for producing hexafluoro-1,3-butadiene.

BACKGROUND ART

Hexafluoro-1,3-butadiene is useful, for example, as an etching gas for semiconductors. As the production method for hexafluoro-1,3-butadiene, various methods have been known. For example, PTL 1 discloses a method of subjecting 1,2,3,4-tetrachlorohexafluorobutane to dechlorination reaction in dioxane in the presence of magnesium at −78° C. PTL 2 discloses a method of subjecting 1,2,3,4-tetrachlorohexafluorobutane to dechlorination reaction in 2-propanol in the presence of zinc.

CITATION LIST

Patent Literature

PTL 1: WO 2005/23734
PTL 2: JP 5005681 B

SUMMARY OF INVENTION

Technical Problem

The methods disclosed in PTLs 1 and 2, however, may fail to produce hexafluoro-1,3-butadiene at an industrially sufficient level of yield, unfortunately.

The present invention is intended to provide a method capable of producing hexafluoro-1,3-butadiene at an industrially sufficient level of yield.

Solution to Problem

To solve the problems, aspects of the present invention are the following [1] to [6].

[1] A method for producing hexafluoro-1,3-butadiene, the method including conducting a reaction, in a reaction liquid containing a halogenated butane represented by chemical formula, $CF_2X^1$—$CFX^2$—$CFX^3$—$CF_2X^4$ ($X^1$, $X^2$, $X^3$, and $X^4$ are each independently a halogen atom other than a fluorine atom), zinc, and an organic solvent, to eliminate the halogen atoms other than a fluorine atom, $X^1$, $X^2$, $X^3$, and $X^4$, from the halogenated butane, yielding hexafluoro-1,3-butadiene, in which during the reaction, a concentration of a zinc halide generated by the reaction, in the reaction liquid is not more than a solubility of the zinc halide in the organic solvent.

[2] The method for producing hexafluoro-1,3-butadiene according to the aspect [1], in which, in the reaction, an organic solvent is added to the reaction liquid to reduce the concentration of the zinc halide in the reaction liquid.

[3] The method for producing hexafluoro-1,3-butadiene according to the aspect [1], in which in the reaction, a portion of the reaction liquid is extracted, next, from an extraction liquid as the extracted reaction liquid, some or all of a dissolved zinc halide is removed, and the extraction liquid from which the zinc halide has been removed is returned to the original reaction liquid to reduce the concentration of the zinc halide in the reaction liquid.

[4] The method for producing hexafluoro-1,3-butadiene according to any one of the aspects [1] to [3], in which the organic solvent is an alcohol.

[5] The method for producing hexafluoro-1,3-butadiene according to the aspect [4], in which the alcohol is at least one of methanol, ethanol, 1-propanol, and 2-propanol.

[6] The method for producing hexafluoro-1,3-butadiene according to any one of the aspects [1] to [5], in which each of $X^1$, $X^2$, $X^3$, and $X^4$ is a chlorine atom.

Advantageous Effects of Invention

According to the present invention, hexafluoro-1,3-butadiene can be produced at an industrially sufficient level of yield.

DESCRIPTION OF EMBODIMENTS

An embodiment of the present invention will now be described. The present embodiment is merely an example of the present invention, and the present invention is not limited to the present embodiment. Various modifications or improvements can be made in the present embodiment, and such various modifications and improvements can be encompassed by the present invention.

In a conventional method for producing hexafluoro-1,3-butadiene, a reaction is conducted in a reaction liquid containing a halogenated butane represented by chemical formula, $CF_2X^1$—$CFX^2$—$CFX^3$—$CF_2X^4$ ($X^1$, $X^2$, $X^3$, and $X^4$ are each independently a halogen atom other than a fluorine atom), zinc, and an organic solvent, to eliminate the halogen atoms other than a fluorine atom, $X^1$, $X^2$, $X^3$, and $X^4$, from the halogenated butane, yielding hexafluoro-1,3-butadiene.

As the reaction proceeds, a metal halide is generated together with hexafluoro-1,3-butadiene, and the generated metal halide is dissolved in the reaction liquid. Accordingly, the concentration of the zinc halide dissolved in the reaction liquid increases as the reaction proceeds. When the concentration of the zinc halide in the reaction liquid exceeds the solubility (saturated concentration) of the zinc halide in the organic solvent, the zinc halide precipitates from the reaction liquid. The inventors of the present invention have found that the precipitated zinc halide interferes with the reaction between the halogenated butane and zinc to reduce the reaction rate of the reaction of yielding hexafluoro-1,3-butadiene, and accordingly the yield decreases.

The reason why the precipitated zinc halide interferes with the reaction between the halogenated butane and zinc is unclear, but is assumed that the unreacted zinc interacts with the precipitated zinc halide, then the zinc surface is covered with the zinc halide, and this interferes with the reaction between the halogenated butane and zinc.

At a higher reaction temperature, the reaction of yielding hexafluoro-1,3-butadiene can proceed at a higher reaction rate, but the precipitated zinc halide gives a large adverse effect, and it is thus difficult to sufficiently improve the reaction rate. In addition, a higher reaction temperature accelerates side reactions, and impurities (by-products) may be generated in larger amounts, unfortunately. Examples of the impurities (by-products) generated at a higher reaction temperature include polymers of hexafluoro-1,3-butadiene, such as a dimer and a trimer thereof.

The inventors of the present invention have carried out intensive studies and consequently have found that when a reaction is conducted while the concentration of a zinc halide in a reaction liquid is maintained to be not more than the solubility (saturated concentration) of the zinc halide in the organic solvent during the reaction, the zinc halide can be prevented from precipitating from the reaction liquid in the reaction, thus the reaction between a halogenated butane and zinc is not inhibited, and the reaction of yielding hexafluoro-1,3-butadiene proceeds at a high reaction rate.

In other words, a method for producing hexafluoro-1,3-butadiene of the present embodiment includes conducting a reaction, in a reaction liquid containing a halogenated butane represented by chemical formula, $CF_2X^1$—$CFX^2$—$CFX^3$—$CF_2X^4$ ($X^1$, $X^2$, $X^3$, and $X^4$ are each independently a halogen atom other than a fluorine atom), zinc, and an organic solvent, to eliminate the halogen atoms other than a fluorine atom, $X^1$, $X^2$, $X^3$, and $X^4$, from the halogenated butane, yielding hexafluoro-1,3-butadiene. In the method, during the reaction, the concentration of a zinc halide generated by the reaction, in the reaction liquid is not more than the solubility of the zinc halide in the organic solvent.

According to the method for producing hexafluoro-1,3-butadiene of the present embodiment, hexafluoro-1,3-butadiene can be produced at an industrially sufficient level of yield (for example, 90% or more). In addition, the reaction rate of the reaction of yielding hexafluoro-1,3-butadiene is high, and thus hexafluoro-1,3-butadiene can be produced efficiently.

Moreover, the reaction is not necessarily conducted at a high temperature, thus side reactions are suppressed, and the amounts of impurities can be reduced. Accordingly, the amount of discharged industrial wastes can be reduced. Hence, the method for producing hexafluoro-1,3-butadiene of the present embodiment enables economic production of hexafluoro-1,3-butadiene.

The amounts of hexafluoro-1,3-butadiene generated as the main product and polymers of hexafluoro-1,3-butadiene generated as by-products can be determined by an analytical method such as gas chromatography and liquid chromatography. From the analysis result, the yield, the purity, and the reaction rate of hexafluoro-1,3-butadiene, the content percentages of impurities, and the like can be calculated.

In the present invention, "precipitation of a zinc halide" means that the state of a zinc halide dissolved in a reaction liquid cannot be maintained, and a fine powder-like solid or a gum-like solid is formed and separated from a reaction liquid. In the present invention, "hexafluoro-1,3-butadiene" means "1,1,2,3,4,4-hexafluoro-1,3-butadiene".

Hereinafter, the method for producing hexafluoro-1,3-butadiene of the present embodiment will be described in further detail with reference to a reaction conducted using a metal reaction container such as an SUS container equipped with a stirrer and a heating jacket.

The halogenated butane usable in the method for producing hexafluoro-1,3-butadiene of the present embodiment may be any type, and $X^1$, $X^2$, $X^3$, and $X^4$ are each independently a halogen atom other than a fluorine atom and may be any of a chlorine atom, a bromine atom, and an iodine atom.

All of $X^1$, $X^2$, $X^3$, and $X^4$ may be the same halogen atom, or some may be the same, and the others may be different halogen atoms. For example, 1,2,3,4-tetrachlorohexafluorobutane in which each of $X^1$, $X^2$, $X^3$, and $X^4$ is a chlorine atom (hereinafter also called "HFTCB") can be used as the halogenated butane. HFTCB is excellent in easy availability and economic efficiency.

The organic solvent may be any type that does not interfere with the progress of dehalogenation reaction of eliminating the halogen atoms other than a fluorine atom, $X^1$, $X^2$, $X^3$, and $X^4$, from the halogenated butane to yield hexafluoro-1,3-butadiene. The organic solvent preferably has poor reactivity with zinc, does not have a zinc halide solubility of 0, and has sufficient dispersibility of zinc. For example, an alcohol, a cyclic ether, acetone, acetonitrile, an aromatic hydrocarbon, an amide solvent, an organic acid, or a mixed solvent of them can be used.

Examples of the alcohol include at least one of methanol, ethanol, 1-propanol, and 2-propanol. Of them, 2-propanol is most preferred from the viewpoint of handling properties.

Examples of the cyclic ether include tetrahydrofuran and dioxane. Examples of the aromatic hydrocarbon include benzene and toluene. Examples of the amide solvent include N,N-dimethylformamide. Examples of the organic acid include acetic acid. Of these organic solvents, an alcohol appropriately helps the dehalogenation reaction to proceed and thus is preferred.

The shape of the zinc is not specifically limited as long as the dehalogenation reaction proceeds, but is preferably a powder form or a ribbon form, and is more preferably a powder form from the viewpoint of reactivity or handling properties. A powder zinc preferably has an average particle diameter of 0.04 mm or more and 10.0 mm or less.

To conduct the above dehalogenation reaction, zinc is first placed in a reaction container, and an organic solvent is added thereto. At the time of placing (at the start of the reaction), the mass ratio of the zinc used to the organic solvent used ([the amount of the zinc used]/[the amount of the organic solvent used]) may be in a range of 0.2 or more and 2.0 or less.

Next, the placed zinc and the organic solvent are mixed, then the temperature is set at typically 20° C. or more and 150° C. or less and preferably 30° C. or more and 95° C. or less, and the pressure is set at typically 0.05 MPa or more and 1 MPa or less in terms of absolute pressure. Then, while the temperature and the pressure are maintained at the above values, a halogenated butane can be gradually added by using a pump or the like. This operation enables the dehalogenation reaction of eliminating halogen atoms other than a fluorine atom from the halogenated butane to generate hexafluoro-1,3-butadiene.

The mass ratio of the halogenated butane used to the zinc used ([the amount of the halogenated butane used]/[the amount of the zinc used]) may be in a range of 1 or more and 12 or less.

As the dehalogenation reaction proceeds, hexafluoro-1,3-butadiene is generated, and a zinc halide is also generated. The zinc halide can be dissolved in the organic solvent, and thus the generated zinc halide is dissolved in the reaction liquid at the initial stage of the dehalogenation reaction. As the dehalogenation reaction proceeds, the concentration of the zinc halide dissolved in the reaction liquid increases. When the concentration of the zinc halide in the reaction liquid exceeds the solubility (saturated concentration) of the zinc halide in the organic solvent, the zinc halide may precipitate from the reaction liquid.

In the reaction, whether or not a zinc halide precipitates from a reaction liquid can be determined by experimentally examining whether or not a mixture (i.e. a reaction liquid) of a halogenated butane, an organic solvent, hexafluoro-1,3-butadiene, and a zinc halide is in a dissolved state at a reaction temperature.

The solubility of a zinc halide in a halogenated butane or hexafluoro-1,3-butadiene is small, and thus the solubility of a zinc halide in an organic solvent can be typically considered as the solubility of a zinc halide in a reaction liquid. Hence, when the reaction is conducted while the concentration of a zinc halide in a reaction liquid is maintained to be not more than the solubility (saturated concentration) of the zinc halide in an organic solvent, the zinc halide can be prevented from precipitating from the reaction liquid in the reaction. The amount of a zinc halide generated can be previously estimated, and thus the type and the amount of an organic solvent can be appropriately selected.

Let us assume that the conversion ratio of a halogenated butane into hexafluoro-1,3-butadiene is 100%. In the reaction, C1/C0 is preferably maintained at 0.1 or more and 1 or less and more preferably maintained at 0.6 or more and 0.8 or less where C1 is the concentration of a zinc halide calculated from the estimated amount of the zinc halide and the amount of an organic solvent in a reaction container, and C0 is the solubility (saturated concentration) of the zinc halide in the organic solvent at a reaction temperature. The amount of a zinc halide in a reaction liquid can be determined by chelatometric titration of the reaction liquid with ethylenediaminetetraacetic acid or the like.

Examples of the method of maintaining the concentration of a zinc halide in a reaction liquid to be not more than the solubility (saturated concentration) of the zinc halide in an organic solvent include a method of conducting the reaction in which a halogenated butane or zinc is set at a low concentration. However, this method is poor in production efficiency, and thus examples of the other method include the following two methods.

The first method is a method in which an organic solvent is added to the reaction liquid in the reaction to reduce the concentration of a zinc halide in the reaction liquid. As the dehalogenation reaction proceeds, the concentration of a zinc halide dissolved in a reaction liquid increases, thus a separately prepared organic solvent is added to the reaction liquid in the reaction, as needed, to reduce the reaction liquid, and the concentration of the zinc halide in the reaction liquid is maintained to be not more than the solubility (saturated concentration) of the zinc halide in the organic solvent. By the first method, the concentrations of a halogenated butane and zinc can be set at high in a reaction liquid at the initial stage of the reaction, and thus a high reaction rate can be achieved.

The second method is a method in which a portion of the reaction liquid is extracted in the reaction, then from an extraction liquid as the extracted reaction liquid, some or all of the zinc halide dissolved therein is removed, and the extraction liquid from which the zinc halide has been removed is returned to the original reaction liquid to reduce the concentration of the zinc halide in the reaction liquid.

The reaction liquid is preferably extracted such that no zinc is contained in the extraction liquid. For example, a supernatant liquid of the reaction liquid is preferably extracted, or the reaction liquid is preferably extracted while the reaction liquid is filtered through a filter.

The method of removing a zinc halide from an extraction liquid is not limited to particular methods, and examples include a method in which an extraction liquid is cooled to precipitate a zinc halide, and the zinc halide is removed by sedimentation, filtration, or a similar method.

Such an extraction liquid containing a zinc halide at a lower content as above is returned to the reaction liquid in the reaction container to reduce the reaction liquid as needed, and the concentration of the zinc halide in the reaction liquid is maintained to be not more than the solubility (saturated concentration) of the zinc halide in the organic solvent.

The solubility of a zinc halide in an organic solvent varies with temperatures. The dissolution amount data of zinc chloride ($ZnCl_2$) in 100 g of 2-propanol are as follows, for reference: 5.9 g at 25° C.; 17.7 g at 40° C.; 30.0 g at 50° C.; 66.1 g at 70° C.; and 120.5 g at 90° C.

Between the concentration of a zinc halide in a reaction liquid and the reaction rate of a dehalogenation reaction, a negative correlation is observed, and as the concentration of a zinc halide increases, the reaction rate decreases. For example, when HFTCB is used as a halogenated butane, and the concentration of zinc chloride in the reaction liquid is the saturated concentration, the reaction rate is 0.08 kg/hr/m$^2$, when the concentration of zinc chloride is 50% of the saturated concentration, the reaction rate is 5.92 kg/hr/m$^2$, and when the concentration of zinc chloride is 0% of the saturated concentration, the reaction rate is 8.83 kg/hr/m$^2$. In the description, the reaction rate means the mass (kg) of HFTCB consumed per unit surface area (m$^2$) of zinc per unit time (H).

After completion of the dehalogenation reaction, the reaction liquid may be treated by a common means such as filtration and distillation to separate a zinc halide or an organic solvent, and hexafluoro-1,3-butadiene may be isolated and purified. Next, hexafluoro-1,3-butadiene may be analyzed to determine the purity, the yield, or the like.

EXAMPLES

The present invention will next be described in further detail with reference to examples and comparative examples.

Example 1

In an SUS 316 autoclave having an internal volume of 500 mL, 119 g of 2-propanol as an organic solvent and 82.4 g of granular metal zinc were placed. The autoclave had a jacket with a cooling structure and a stirrer at the upper part, and the heating system was a jacket heating system.

While the content in the autoclave was stirred, the temperature was increased to 70° C. To the outlet of the autoclave, a Dimroth condenser was attached. While the content in the autoclave was maintained at a temperature of 70° C. under normal pressure, 149 g of 1,2,3,4-tetrachloro-hexafluorobutane was added dropwise at a drop rate of 9.31 g per hour and was reacted. After 10 hours of dropwise addition, 100 g of 2-propanol was further added to the content, and the dropwise addition of 1,2,3,4-tetrachloro-hexafluorobutane was further continued.

After completion of the dropwise addition for 16 hours in total, the reaction was conducted for 2 hours while the temperature of the content was maintained at 70° C. During the reaction, no precipitation of zinc chloride from the content in the autoclave was observed.

After completion of the reaction for 2 hours, the reaction product was further heated to a temperature around the boiling point of 2-propanol, thus a portion of the organic solvent (2-propanol) and the product were vaporized, and the vapor of them was cooled, liquified, and collected by using a trap cooled by a mixture of dry ice and ethanol. The crude yield was then calculated from the collected product to be 99%. The collected product was analyzed by gas chromatography, and the yield of hexafluoro-1,3-butadiene was 90%.

In the description, the crude yield and the yield are defined by the following formulae.

Crude yield (%)=[(mass of collected product liquified and collected])/(mass when charged HFTCB is completely converted into hexafluoro-1,3-butadiene)]×100

Yield (%)=(the above crude yield)×(content percentage of hexafluoro-1,3-butadiene in collected product determined by GC analysis)

Example 2

In an SUS 316 autoclave having an internal volume of 500 mL, 119 g of 2-propanol as an organic solvent and 82.4 g of granular metal zinc were placed. The autoclave had a jacket with a cooling structure and a stirrer at the upper part, and the heating system was a jacket heating system.

While the content in the autoclave was stirred, the temperature was increased to 70° C. While the content in the autoclave was maintained at a temperature of 70° C. under normal pressure, 149 g of 1,2,3,4-tetrachlorohexafluorobutane was added dropwise at a drop rate of 9.31 g per hour and was reacted. In the reaction, the following operation was performed: a portion of the content (reaction liquid) was extracted from the autoclave and was cooled to room temperature to precipitate the dissolved zinc chloride, thus 127 g of zinc chloride was removed from the content, and the residual content was returned into the autoclave. After completion of the dropwise addition of 1,2,3,4-tetrachlorohexafluorobutane for 16 hours in total, the reaction was conducted for 2 hours while the temperature of the content was maintained at 70° C. During the reaction, no precipitation of zinc chloride from the content in the autoclave was observed.

After completion of the reaction for 2 hours, the reaction product was further heated to a temperature around the boiling point of 2-propanol, thus a portion of the organic solvent (2-propanol) and the product were vaporized, and the vapor of them was cooled, liquified, and collected by using a trap cooled by a mixture of dry ice and ethanol. The crude yield was then calculated from the collected product to be 99%. The collected product was analyzed by gas chromatography, and the yield of hexafluoro-1,3-butadiene was 92%. The crude yield and the yield are as defined above.

Comparative Example 1

In an SUS 316 autoclave having an internal volume of 500 mL, 119 g of 2-propanol as an organic solvent and 82.4 g of granular metal zinc were placed. The autoclave had a jacket with a cooling structure and a stirrer at the upper part, and the heating system was a jacket heating system.

While the content in the autoclave was stirred, the temperature was increased to 70° C. While the content in the autoclave was maintained at a temperature of 70° C. under normal pressure, 149 g of 1,2,3,4-tetrachlorohexafluorobutane was added dropwise at a drop rate of 9.31 g per hour and was reacted.

After completion of the dropwise addition of 1,2,3,4-tetrachlorohexafluorobutane for 16 hours in total, the content was heated to a temperature of 90° C., and the reaction was conducted for 5 hours while the temperature was maintained at 90° C. In the reaction at 70° C., precipitation of zinc chloride from the content in the autoclave was observed.

After completion of the reaction for 5 hours, the reaction product was further heated to a temperature around the boiling point of 2-propanol, thus a portion of the organic solvent (2-propanol) and the product were vaporized, and the vapor of them was cooled, liquified, and collected by using a trap cooled by a mixture of dry ice and ethanol. The crude yield was then calculated from the collected product to be 97%. The collected product was analyzed by gas chromatography, and the yield of hexafluoro-1,3-butadiene was 80%. The crude yield and the yield are as defined above.

The invention claimed is:

1. A method for producing hexafluoro-1,3-butadiene, the method comprising:
   conducting a reaction, in a reaction liquid containing a halogenated butane represented by chemical formula $CF_2X^1$-$CFX^2$-$CFX^3$-$CF_2X^4$ ($X^1$, $X^2$, $X^3$, and $X^4$ are each independently a chlorine atom, a bromine atom or an iodine atom), zinc, and an organic solvent selected from the group consisting of an alcohol, a cyclic ether, acetone, acetonitrile, an aromatic hydrocarbon, an amide solvent, an organic acid, and a mixed solvent thereof, to eliminate $X^1$, $X^2$, $X^3$, and $X^4$, which are selected from the group consisting of the chlorine atom, the bromine atom and the iodine atom, from the halogenated butane, yielding hexafluoro-1,3-butadiene, wherein
   during the reaction, a concentration of a zinc halide generated by the reaction in the reaction liquid is not more than a solubility of the zinc halide in the organic solvent, and
   as the reaction proceeds, an organic solvent is added to the reaction liquid to reduce the concentration of the zinc halide in the reaction liquid.

2. The method for producing hexafluoro-1,3-butadiene according to claim 1, wherein the organic solvent is an alcohol.

3. The method for producing hexafluoro-1,3-butadiene according to claim 2, wherein the alcohol is at least one of methanol, ethanol, 1-propanol, and 2-propanol.

4. The method for producing hexafluoro-1,3-butadiene according to claim 2, wherein each of $X^1$, $X^2$, $X^3$, and $X^4$ is a chlorine atom.

5. The method for producing hexafluoro-1,3-butadiene according to claim 3, wherein each of $X^1$, $X^2$, $X^3$, and $X^4$ is a chlorine atom.

6. The method for producing hexafluoro-1,3-butadiene according to claim 1, wherein each of $X^1$, $X^2$, $X^3$, and $X^4$ is a chlorine atom.

7. A method for producing hexafluoro-1,3-butadiene, the method comprising:
   conducting a reaction, in a reaction liquid containing a halogenated butane represented by chemical formula $CF_2X^1$-$CFX^2$-$CFX^3$-$CF_2X^4$ ($X^1$, $X^2$, $X^3$, and $X^4$ are each independently a chlorine atom, a bromine atom or an iodine atom), zinc, and an organic solvent selected from the group consisting of an alcohol, a cyclic ether, acetone, acetonitrile, an aromatic hydrocarbon, an amide solvent, an organic acid, and a mixed solvent thereof, to eliminate $X^1$, $X^2$, $X^3$, and $X^4$, which are selected from the group consisting of the chlorine atom, the bromine atom and the iodine atom, from the halogenated butane, yielding hexafluoro-1,3-butadiene, wherein during the reaction, a concentration of a zinc halide generated by the reaction in the reaction liquid is not more than a solubility of the zinc halide in the organic solvent, and in the reaction, steps include:

extracting a portion of the reaction liquid to provide an extraction liquid as the extracted reaction liquid, removing some or all of the dissolved zinc halide from the extraction liquid, and returning the extraction liquid from which the zinc halide has been removed to the original reaction liquid to reduce the concentration of the zinc halide in the reaction liquid.

8. The method for producing hexafluoro-1,3-butadiene according to claim 7, wherein the organic solvent is an alcohol.

9. The method for producing hexafluoro-1,3-butadiene according to claim 7, wherein each of $X^1$, $X^2$, $X^3$, and $X^4$ is a chlorine atom.

* * * * *